United States Patent [19]

Adams

[11] 4,219,912
[45] Sep. 2, 1980

[54] INJECTION SITE HAVING THERMOPLASTICALLY SEALED INJECTION PORT

[75] Inventor: Elvis E. Adams, Downers Grove, Ill.

[73] Assignee: Baxter Travenol Laboratories, Inc., Deerfield, Ill.

[21] Appl. No.: 949,881

[22] Filed: Oct. 10, 1978

[51] Int. Cl.³ .............................................. A61M 5/00
[52] U.S. Cl. .............................. 128/214 G; 128/214.2; 215/232; 215/247; 156/73.1
[58] Field of Search ............ 128/214 R, 214 G, 214.2, 128/247; 215/232, 247, 274, 355; 156/73.1

[56] References Cited

U.S. PATENT DOCUMENTS

| | | | |
|---|---|---|---|
| 3,900,028 | 8/1975 | McPhee | 128/272 |
| 4,046,610 | 9/1977 | Lilja | 156/73.1 |
| 4,048,995 | 9/1977 | Mittleman | 128/214 G |
| 4,048,996 | 9/1977 | Mittleman | 128/214 G |
| 4,133,441 | 1/1979 | Mittleman et al. | 215/247 |

FOREIGN PATENT DOCUMENTS 2656800 7/1977 Fed. Rep. of Germany .......... 156/73.1

*Primary Examiner*—Dalton L. Truluck
*Attorney, Agent, or Firm*—H. W. Collins; Paul C. Flattery; Raymond Mehler

[57] ABSTRACT

Injection sites are provided for injecting substances such as medicaments into systems that are feeding parenteral fluid to a patient, which injection sites have injection ports that are thermoplastically sealed into the injection site in a manner that is simpler, faster, less expensive, and more readily automated than other assemblies. The assembly includes a vibratory energy seal of the non-thermoplastic port within a countersunk thermoplastic seat.

17 Claims, 8 Drawing Figures

U.S. Patent  Sep. 2, 1980  Sheet 1 of 2  4,219,912
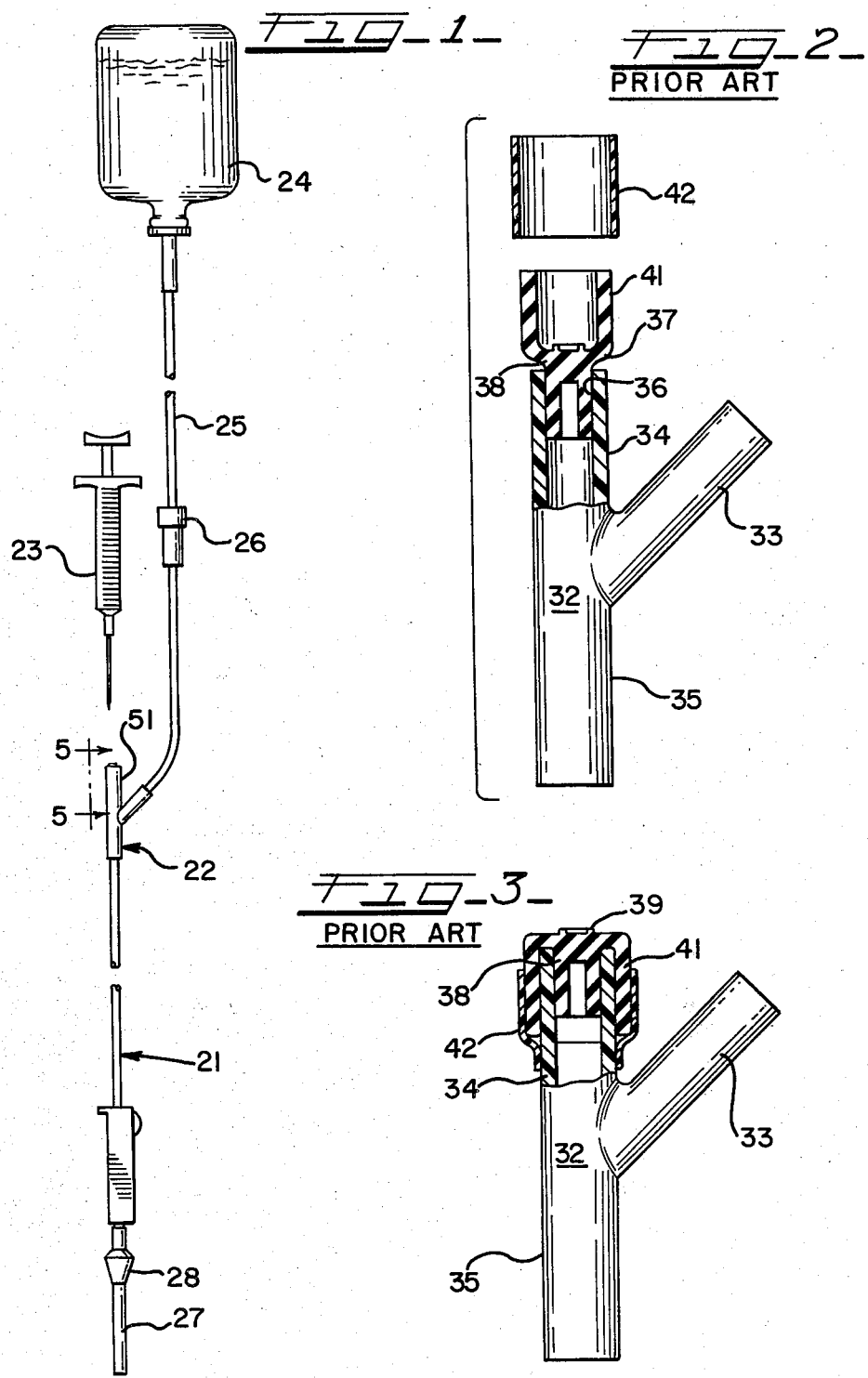

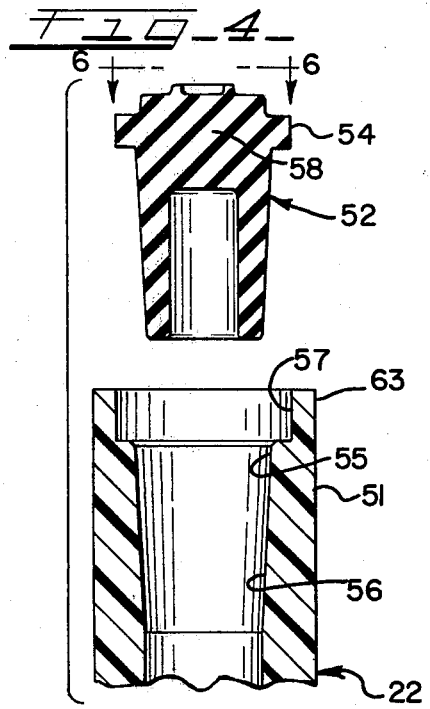
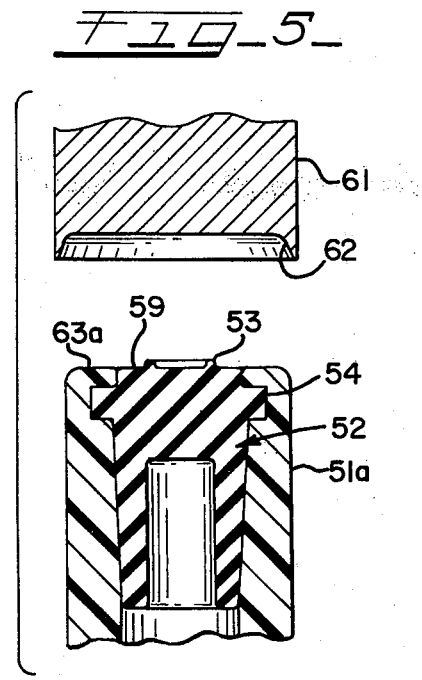
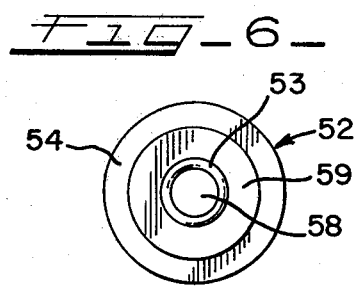
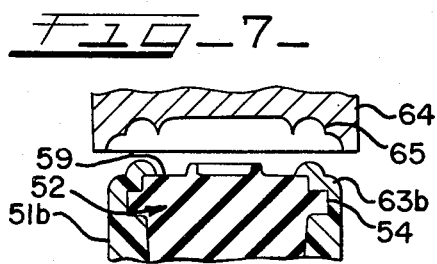
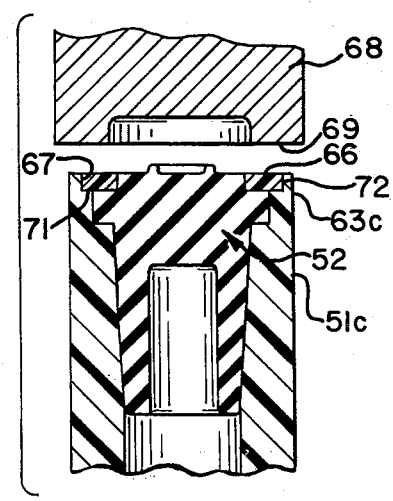

INJECTION SITE HAVING THERMOPLASTICALLY SEALED INJECTION PORT

BACKGROUND AND DESCRIPTION OF THE INVENTION

The present invention relates generally to improvements in injection sites and more particularly to certain improvements which enhance the assembly and sealing of injection ports into injection sites along tubing for parenterally administering fluids to patients. More particularly, the invention includes an injection port of a particular construction that is sealed with vibratory energy at a specially configured injection site by techniques accomplishing swaging, butt sealing and/or shear sealing.

Several different types and structures of injection sites are shown in patents such as Brody U.S. Pat. No. 3,332,418, Mittleman U.S. Pat. No. 4,000,740 and No. 4,048,995, and Mittleman et al. U.S. Pat. No. 4,048,996, each of which is incorporated by reference herein. By such devices, it is possible to introduce a supplementary fluid such as a medicament, whole blood or blood fraction into the stream of an intravenous or other parenteral type of package or of an anesthesiology administration set that has been contructed with a branched site having an injection port sealed thereon, which port is rupturable or pierceable by a hypodermic needle to permit the supplementary fluid to enter the stream without interrupting its flow, ports of this type usually being selfsealing to the extent that the site generally will not leak after they are pierced by a hypodermic needle. Port materials that exhibit these highly advantageous properties are typically not thermoplastic and will be deformed and damaged by most sealing operations; yet, these ports must be hermetically sealed at the correct location on the injection site in order to meet the needs and requirements of the parenteral medical package.

An important prior art approach to sealing these delicate injection ports, illustrated in Brody U.S. Pat. No. 3,332,418, uses a heat shrinkable band to hold down an external, overlapping skirt portion of this injection port. This approach is cumbersome, labor intensive, and not particularly well suited to automated operations. A need to use shrink tubing is avoided by structures such as U.S. Pat. No. 4,000,740, No. 4,048,995 and No. 4,048,996, which illustrate a significantly different assembly method. In these patents, the injection ports are inserted into segmented portions of the injection site body, and then those segmented portions are assembled and bonded by, for example, sonic welding while being very careful to try and maintain proper location of the various parts and to avoid pinching or other damage to the injection port.

Bonding of materials together by using a vibratory means, is discussed, for example, in Bieber U.S. Pat. No. 3,972,758 and in Lilja U.S. Pat. No. 4,046,610, incorporated by reference herein. Such bonding techniques can include swaging, butt bonding, or shear bonding. Swaging, as the term is used herein, refers to the use of an ultrasonic or other vibratory energy horn having a generally concave working surface that applies, in addition to vibratory energy, a directing force or pressure upon a projection of a thermoplastic body in order to reform that projection to a desired shape for the purpose, for example, of bending that projection over to shape it as an edge to hold an item onto the thermoplastic body. Generally, butt bonding involves applying a flat surface of a vibratory energy horn to the flat surface of a thermoplastic part to be bonded to another thermoplastic part butting thereagainst in order to fuse the one part onto the other. In shear bonding, vibratory forces are transmitted to a location to be bonded so as to develop shear forces along the bond locations, typically by applying a flat-surfaced vibratory horn perpendicularly to the bond location.

By the present invention, there are eliminated the assembly disadvantages either of having to fold over a skirt portion of an injection port and then hold it in place by a tubing that is shrunk therearound or of having to bond together a segmented injection site structure while maintaining each injection port at its intended final location during bonding. In accordance with the present invention, an injection site that has previously been formed or bonded into a single-piece, unsegmented structure has a specially structured pierceable port installed therewithin without having to use a shrink tubing or the like. The delicate pierceable injection port is passed into a seat having a particular construction and located within the branched portion of an injection site device, and this port is then encapsulated therewithin by the application of vibratory energy.

It is accordingly a general object of the present invention to provide an improved injection site within a parenteral fluid delivery system.

Another object of the invention is an improved method of sealing a pierceable injection port within a thermoplastic injection site while avoiding the assembly disadvantages associated with shrink tubing and with the simultaneous assembly of multiple components.

Another object of the present invention is an improved injection site in a parenteral fluid delivery system that is easily assembled in a manner readily susceptible to automation and that exhibits improvements in being able to be quickly assembled without misalignment of or damage to the flexible, pierceable injection port.

Another object of this invention is the improved use of ultrasonic energy or the like for encapsulating a pierceable injection port at its desired location in an injection site of a parenteral fluid delivery system.

These and other objects of the present invention will be apparent from the following detailed description taken in conjunction with the accompanying drawings, wherein:

FIG. 1 is an elevational view of a parenteral fluid delivery system having an injection site in accordance with this invention;

FIG. 2 is an enlarged elevational view, partially in cross-section, of a prior art injection site in a partially assembled state;

FIG. 3 is an elevational view of the prior art injection site of FIG. 2, after it has been fully assembled;

FIG. 4 is an enlarged longitudinal cross-sectional view of the preferred embodiment of this invention prior to assembly thereof;

FIG. 5 is an enlarged sectional view of the preferred embodiment of this invention after assembly, taken along the line 5—5 of FIG. 1, and shown together with a cross-section of the working end of the ultrasonic horn used during assembly of this preferred embodiment;

FIG. 6 is a plan view of the preferred injection port, taken along the line 6—6 of FIG. 4;

FIG. 7 is a longitudinal cross-sectional view of an alternative embodiment after encapsulating the preferred injection port within an injection site, shown together with a cross-section of the working end of the horn used during assembly of this alternative embodiment; and FIG. 8 is a longitudinal cross-sectional view of another alternative embodiment which includes a supplementary ring for sealing an injection port into an injection site, shown together with a cross-section of the working end of the horn used during assembly of this embodiment.

A parenteral fluid delivery system, depicted generally at 21 is illustrated in FIG. 1 with an injection site, generally designated 22, in accordance with this invention. Also shown is a hypodermic needle 23 poised for penetration into the injection site 22. Parenteral fluid is stored within container 24 for passage through tubing 25, filter 26, the injection site 22, and into the patient by suitable means such as through a disposable needle 27, protected by a transparent shroud 28 prior to use. The parenteral fluid within the system may be an intravenous solution, a medicament, whole blood, or portions of whole blood, while the fluid within the hypodermic needle 23 may be a similar fluid, and is most typically a medicament for introduction into an intraveneous food solution within the system 21. By such an arrangement, it is possible to treat a patient simultaneously with more than one fluid. Such systems also reduce the number of times that the patient must be punctured when multiple treatments are necessary.

A prior art injection site, generally depicted at 32, is shown in FIGS. 2 and 3. This particular injection site 32 is a Y-site that is branched into a parenteral fluid passageway branch 33 and an injection branch 34, both opening into a common conduit 35. Such injection sites, both in the prior art and according to the present invention, may take any one of several general configurations which provide, in essence, two passageways merging into a single passageway for passing two or more different fluids on to the patient. The illustrated injection branch 34 has a straight-walled or non-stepped entry conduit 36 for receiving resilient injection port member 37, including an injection port portion 38 having a guide ring 39 for assisting in properly locating the tip of the hypodermic needle 23 to pass it through the injection port 38 and into the injection branch 34. Port member 37 includes an outwardly projecting resilient and pliable cylindrical skirt portion 41. Port member 37, including its skirt portion 41, is made of a rubbery, nonrigid material which makes it possible, provided adequate care, skill, and effort are used, to roll or fold down over the cylindrical injection branch 34 until it is installed as illustrated in FIG. 3.

Then, after the resilient injection port member 37 is folded upon itself and over the injection branch 34, a length of shrink tubing 42 is slid over the folded down skirt portion 41 until a portion of a shrink tubing 42 extends beyond the skirt portion 41, after which, the tubing 42 is subjected to appropriate heating conditions in order to shrink the length of tubing 42 in place around both the skirt portion 41 and the injection branch 34 for the purpose of sealingly installing the resilient injection port member 37 into the injection site 32.

FIGS. 4, 5, and 6 show further details of the preferred injection site 22 in accordance with this invention. These figures are enlarged views of injection site branch 51 of the injection site 22. Also shown is the preferred injection port plug, illustrated generally by 52, having a guide ring 53 and an annular outwardly projecting boss or lip 54. Injection site branch 51 has a seat 55 including a main bore 56 that is generally cylindrical, although it is typically tapered slightly inwardly in order to facilitate insertion of the injection port plug 52 thereinto. Seat 55, in its unassembled state as depicted in FIG. 4, includes a countersink or enlarged bore 57 at its outside or entry end thereof. Injection port plug 52 further includes a penetrable wall 58 capable of being pierced by hypodermic needle 23, which wall 58 lies between the outside surface 59 of the plug 52 and the interior of the plug 52 opening into main bore 56.

FIG. 5 shows a vibratory energy horn 61 positioned over sealed injection site branch 51a, which is branch 51 after it has been deformed for thermoplastically sealing the injection port plug 52 therein by forces transmitted through and pressures generated by a vibratory energy horn 61. The vibratory energy transmitted by horn 61 is preferably developed by ultrasonic generator means (not shown), which means is of a known construction. Other vibratory energy generating means capable of developing bonding and/or swaging conditions in thermoplastic material may likewise be used.

Horn 61 includes recessed annular working face 62 for transmitting vibratory energy to cylindrical wall 63 of the enlarged bore 57 so as to direct the cylindrical wall 63 inwardly and downwardly in order to form swaged wall 63a over the boss 54 to thermoplastically seal or encapsulate the injection port plug 52 into the sealed injection site branch 51a. This swage is formed by moving the horn 61 over the cylindrical wall 63 of the injection site branch 51 and continuing this movement and the pressure applied to the wall 63 thereby until the desired deformation of wall 63 into swaged wall 63a is accomplished. Thereafter, the horn 61 is moved out of contact with the sealed branch 51a, which stage is shown generally in FIG. 5.

FIG. 7 depicts an alternative embodiment with a sealed injection site branch 51b having an overlapping swaged wall 63b that is deformed and swaged over both the annular boss 54 as well as overlapped over a circumferential edge of the outside surface 59 of port plug 52. This will form an especially advantageous seal by increasing the surface area and number of different surface locations that the swaged thermoplastic wall 63b overlies and resiliently contacts the port plug 52. This alternative swaged wall 63b is formed by the operation of a vibratory energy horn 64 having a recessed annular working face 65 configured so as to direct cylindrical wall 63 being softened by the vibratory energy into the swage overlapping the outside surface 59 of the port plug 52.

Another alternative embodiment shown in FIG. 8, has an injection site branch 51c that generally includes a butt seal and a shear seal while it does not include what can be truly characterized as a swage, since the encapsulating feature of this embodiment includes a ring 66 thermoplastically bonded to a cylindrical wall 63c which includes a second countersink or further enlarged bore 67. Vibratory energy horn 68 has a generally planar annular working face 69 for directly applying vibratory energy to the outside surface of the ring 66 in order to form a butt seal 71 as a radially extending thermoplastic bond between the radially extending surface of bore 67 and the outer annular extent of the inside surface of the ring 66. At the same time, a shear seal 72 is included as a longitudinally extending thermoplastic bond between the outside circumferential edge of the ring 66 and the longitudinally extending circumferential surface of the bore 67, which shear seal can be enhanced by having the outer circumference of ring 66 be equal to or in an oversized condition with respect to the circumference of the further enlarged bore 67.

The method of this invention relates generally to constructing injection sites and further to thermoplastically sealing or encapsulating injection site ports into injection sites for parenteral fluid delivery systems. An injection port plug member is inserted into a countersunk conduit through an injection site branch, and then the plug member is encapsulated into the injection site branch conduit through the use of vibratory energy.

More particularly, the method includes countersinking the end of the conduit within an injection site branch of a parenteral fluid delivery system so as to provide a deformable thermoplastic wall that is typically cylindrical in configuration. An injection port plug member is provided so as to have an outer surface complementary with the inner surface of the injection site branch conduit and its countersink. Preferably, the formation of the complementary surface of the injection port plug member includes outwardly extending a section of its annular surface to form an annular boss or lip thereon. Thereafter, these complementary surfaces are matingly engaged with each other by plugging or sliding the plug member into the conduit until the annular boss abuts against the countersink, after which the plug member is sealed or encapsulated into the conduit.

The sealing or encapsulating step is one that does not damage or significantly deform the injection port plug member, although it can include a limited amount of compression of the port plug member in order to enhance the integrity of the seal while avoiding excessive deformation which would misalign the port plug member sealed within the branch conduit. Such encapsulating or sealing step preferably utilizes a source of vibratory energy, preferably transmitting that energy so as to accomplish a swaging step, although it can also or alternatively include one or both of a butt sealing step or a shear sealing step. In one particular alternative embodiment, there is accomplished an additional step of secondarily countersinking the countersunk injection site branch conduit followed by inserting an annular ring member therein while simultaneously overlapping the outwardly extending annular boss of the injection port plug member with the radially innermost extent of the inside surface of the ring member. Then, the annular ring member is both shear bonded and butt bonded to the inside radial and annular walls of the secondary countersink while in sealing contact with the injection port plug member.

The form of vibratory energy utilized in the sealing or encapsulating step can be that of any suitable system intended for swaging or vibratorily welding thermoplastic materials. Preferably, ultrasonic energy is used. The amount of energy applied, which varies with the thermoplastic material being swaged or welded, can be as high as about 1200 watts. For most thermoplastic materials suitable for this invention, the energy applied will be between about 300 and 900 watts. A suitable apparatus for providing the ultrasonic energy is known in the trade as a 900-Watt Sonic Sealer.

While any thermoplastic material that is acceptable for use in connection with parenteral fluids can be used in forming the injection site branch and the other portions of the injection site, it is preferred to use thermoplastic materials that are not only medical grade but also are readily swaged, are very clearly transparent to permit the observation of tiny bubbles within the injection site, and exhibit solvent bonding characteristics to the extent that the injection site can be securely attached by adhesives or the like to the tubing of the rest of the parenteral fluid delivery system. Acceptable thermoplastic materials, listed in order of general preference, include polycarbonate, styrene acrylonitrile, acrylic, polystyrene, and polyester materials.

Each injection port plug is made of an elastomeric material that is easily punctured by a hypodermic needle and that exhibits resealability characteristics upon withdrawal of the needle. Preferably, the material should also resist full circumferential severance when a hypodermic needle punctures the injection port plug and as it passes therethrough, which property is known as "core resistance". Injection ports made of materials that do not exhibit core resistance will tend to have a cylindrical core cut out of the all 58 by the hypodermic needle, and this cylindrical core will typically cause a restriction or a stoppage of the flow of fluids through the injection site. Acceptable injection port plug materials are isoprene and natural rubber.

It will be apparent to those skilled in this art that the present invention can be embodied in various forms; accordingly, this invention is to be construed and limited only by the scope of the appended claims.

I claim:

1. An injection site for a parenteral fluid delivery system, comprising:

an injection branch of the injection site having a main bore therethrough, said main bore having an outside end and a fluid outlet;

an elastomeric injection port plug having an outside surface including an outside surface of a wall penetrable by a hypodermic needle, said port plug having an annular outwardly projecting boss, said annular outwardly projecting boss being spaced from said outside surface to form an annular step between said outside surface and said boss of the port plug;

a fluid passageway branch of the injection site, said fluid passageway branch having a passageway that opens into said main bore of the injection branch at a location between said injection port plug and said fluid outlet of the main bore of the injection branch;

a thermoplastic seat at said outside end of said main bore of the injection branch, said seat being generally complementary to the outside surface of said injection port plug and said injection port plug being within said seat; and said seat having a seal overlying said annular step of the port plug for encapsulation of said injection port plug except for at least part of said outside surface of the plug, said seat seal being formed by a horn for imparting vibratory energy to said outside end of the main bore of the injection branch, said seat seal including substantially the entirety of said outside end of the main bore.

2. The injection site of claim 1, wherein said seat includes a countersink of the outside end of said main bore, said countersink being for receiving said boss of the injection port plug.

3. The injection site of claim 1, wherein said seat seal is a swaged seal overlying said annular outwardly projecting boss of the elastomeric injection port plug.

4. The injection site of claim 1, wherein said seat seal is a swaged seal overlying said annular outwardly projecting boss and a circumferential edge of said outside surface of the elastomeric injection port plug.

5. The injection site of claim 1, wherein said seat seal includes a ring partially overlying said annular outwardly projecting boss of the elastomeric injection port plug, said seat includes a countersink of the outside end of said main bore, said countersink being for receiving said boss of the injection port plug, said coountersink includes a second countersink therein for receiving said ring, and said seat seal is a vibratory energy butt and shear bond of the ring to said second countersink.

6. In an improved parenteral fluid delivery system including a parenteral fluid storage container; a needle; an injection site having an parenteral fluid inlet, an injection branch having a main bore therethrough for passing a supplementary fluid into the injection site, and a fluid outlet opening into both the parenteral fluid inlet and the branch; and tubing communicating the storage container with the parenteral fluid inlet and communicating the fluid outlet with the needle; the improvement comprising:
an elastomeric injection port plug having an outside surface including an outside surface of a wall penetrable by a hypodermic needle, said port plug having an annular outwardly projecting boss, said annular outwardly projecting boss being spaced from said outside surface to form an annular step between said outside surface and said boss of the port plug;
a thermoplastic seat at the outside end of said main bore of the injection branch, said seat being generally complementary to the outside surface of said injection port plug and said injection port plug being within said seat; and
said seat having a seal overlying said annular step of the port plug for encapsulation of said injection port plug except for at least part of said outside surface of the plug, said seat seal being formed by a horn for imparting vibratory energy to said outside end of the main bore of the injection branch, said seat seal including substantially the entirety of said outside end of the main bore.

7. The parenteral fluid delivery system of claim 6, wherein said seat includes a countersink of the outside end of said main bore, said countersink being for receiving said boss of the injection port plug.

8. The parenteral fluid delivery system of claim 6, wherein said seat seal is a swaged seal overlying said annular outwardly projecting boss of the elastomeric injection port plug.

9. The parenteral fluid delivery system of claim 6, wherein said seat seal is a swaged seal overlying said annular outwardly projecting boss and a circumferential edge of said outside surface of the elastomeric injection port plug.

10. The parenteral fluid delivery system of claim 6, wherein said seat seal includes a ring partially overlying said annular outwardly projecting boss of the elastomeric injection port plug, said seat includes a countersink of the outside end of said main bore, said countersink being for receiving said boss of the injection port plug, said countersink includes a second countersink therein for receiving said ring, and said seat seal is a vibratory energy butt and shear bond of the ring to said second countersink.

11. A method of constructing injection sites for patenteral fluid delivery systems, comprising:
providing an elastomer injection port plug member with an outside surface of a wall penetrable by a hypodermic needle and with an outwardly extending annular boss spaced from said outside surface to form an annular step between said outside surface and said boss;
forming a thermoplastic seat within an injection branch of an injection site having a main bore with an outside end and a fluid outlet therethrough and having a fluid passageway branch opening into said main bore at a location between said injection port plug member and said fluid outlet, said seat being generally complementary to the outside surface of the injection port plug member;
inserting the injection port plug member into the thermoplastic seat; and
encapsulating the injection port plug member except for at least part of the outside surface of the plug member, said encapsulating step including imparting vibratory energy to the outside end of the main bore of the injection branch until said outside end overlies the annular step of the port plug and until said seat seal includes substantially tne entirety of said outside end of the main bore.

12. The method of claim 11, wherein said step of forming a thermoplastic seat includes countersinking the outside end of the main bore to a circumference equal to or less than the circumference of the boss of the injection port plug member.

13. The method of claim 11, wherein said encapsulating step includes swaging the outside end of the thermoplastic seat over the boss of the injection port plug member.

14. The method of claim 11, wherein said encapsulating step includes swaging the outside end of the thermoplastic seat over the boss and over a circumferential edge of the outside surface of the injection port plug member.

15. The method of claim 11, wherein said step of forming a thermoplastic seat includes first countersinking the outside end of the main bore to a circumference equal to or less than the circumference of the boss of the plug member and further countersinking the outside end of the first countersink to a circumference greater than the first countersink, wherein said inserting step includes locating a ring to partially overlie the boss, and wherein said encapsulating step includes butt bonding and shear bonding the ring to the further countersink.

16. The method of claim 11, wherein said encapsulating step includes compressing the boss of the elastomeric plug member to enhance sealing between the seat and the plug member.

17. The method of claim 11, further comprising solvent bonding the injection site to tubing for parenteral fluid delivery systems.

* * * * *